(12) United States Patent
Nitta

(10) Patent No.: US 9,417,173 B2
(45) Date of Patent: Aug. 16, 2016

(54) FINE PARTICLE MEASUREMENT DEVICE, AND LAMINAR FLOW MONITORING METHOD AND FINE PARTICLE ANALYSIS METHOD IN FINE PARTICLE MEASUREMENT DEVICE

(71) Applicant: Sony Corporation, Tokyo (JP)

(72) Inventor: Nao Nitta, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/418,711

(22) PCT Filed: Jun. 5, 2013

(86) PCT No.: PCT/JP2013/065586
§ 371 (c)(1),
(2) Date: Jan. 30, 2015

(87) PCT Pub. No.: WO2014/024556
PCT Pub. Date: Feb. 13, 2014

(65) Prior Publication Data
US 2015/0177113 A1    Jun. 25, 2015

(30) Foreign Application Priority Data

Aug. 7, 2012   (JP) .................................. 2012-175214

(51) Int. Cl.
| | |
|---|---|
| *G01N 21/00* | (2006.01) |
| *G01N 11/02* | (2006.01) |
| *G01N 21/21* | (2006.01) |
| *G01N 21/64* | (2006.01) |
| *G01N 15/14* | (2006.01) |
| *G01N 21/53* | (2006.01) |
| *G01F 1/66* | (2006.01) |
| *G01N 15/10* | (2006.01) |
| *G01N 11/00* | (2006.01) |
| *G01N 21/47* | (2006.01) |

(52) U.S. Cl.
CPC ............... *G01N 11/02* (2013.01); *G01F 1/661* (2013.01); *G01N 15/1404* (2013.01); *G01N 15/1459* (2013.01); *G01N 21/21* (2013.01); *G01N 21/53* (2013.01); *G01N 21/64* (2013.01); *G01N 2011/008* (2013.01); *G01N 2015/1006* (2013.01); *G01N 2015/1415* (2013.01); *G01N 2021/4792* (2013.01); *G01N 2021/6417* (2013.01); *G01N 2021/6493* (2013.01)

(58) Field of Classification Search
CPC .................. G01N 2015/1006; G01N 21/6428; G01N 15/1484; G01N 15/1434; G01N 15/1459; G01N 15/147; G01N 2015/149; G01N 33/5091; G01N 15/1429; G01N 2035/00326; G01N 21/6486; G01N 33/5005; G01N 15/1404
See application file for complete search history.

(56) References Cited

U.S. PATENT DOCUMENTS

2012/0050737 A1    3/2012   Dowaki et al.

FOREIGN PATENT DOCUMENTS

| CN | 102192872 A | 9/2011 |
|---|---|---|
| CN | 102401776 A | 4/2012 |
| CN | 102564929 A | 7/2012 |
| JP | 62-036541 A | 2/1987 |
| JP | 02-304333 A | 12/1990 |
| JP | 08-304263 A | 11/1996 |
| JP | 09-166541 A | 6/1997 |
| JP | 2011-149822 A | 8/2011 |

*Primary Examiner* — Michael P Stafira
(74) *Attorney, Agent, or Firm* — Wolf, Greenfield & Sacks, P.C.

(57) ABSTRACT

There is provided a laminar flow monitoring method in a fine particle measurement device, the method including a radiation step of radiating light to a laminar flow, a position detection step of receiving, by a detector, an S polarized component which is separated from scattered light produced from the laminar flow and to which astigmatism is given and acquiring light reception position information of the S polarized component in the detector, and a determination step of determining a state of the laminar flow based on the light reception position information.

19 Claims, 17 Drawing Sheets

FIG. 6
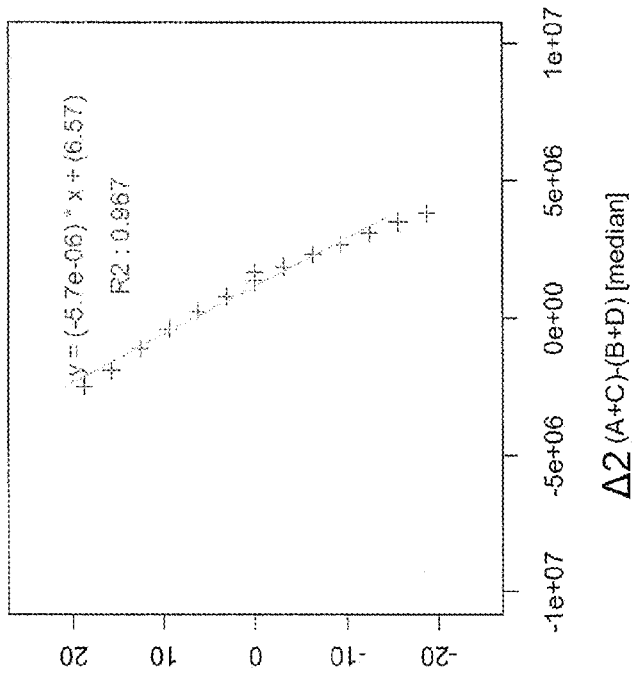
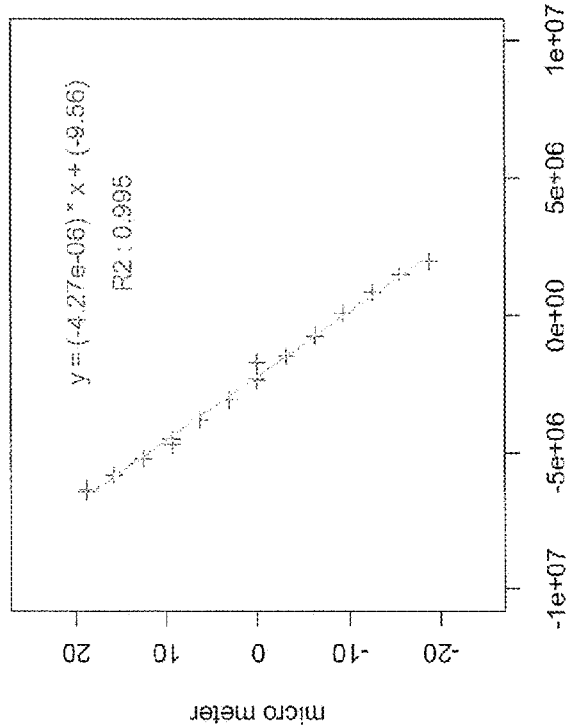

FIG. 9
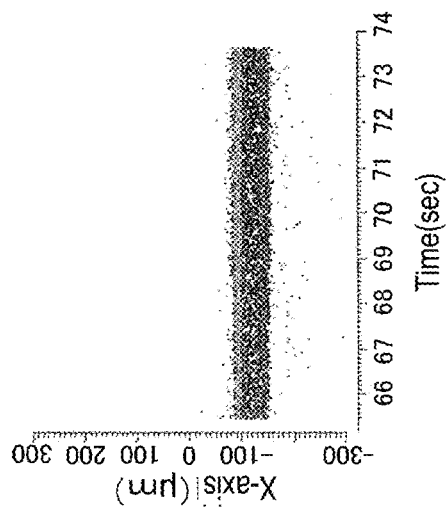
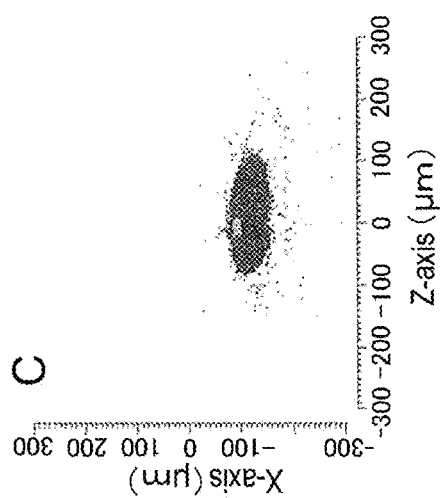
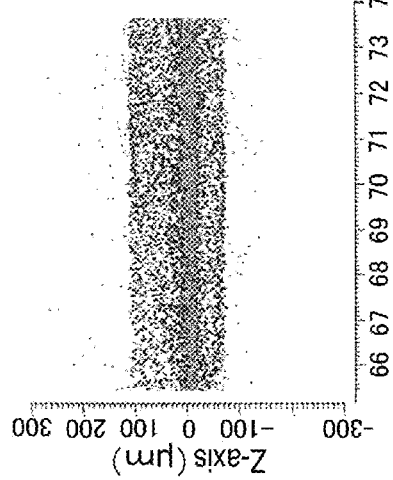

FIG. 12
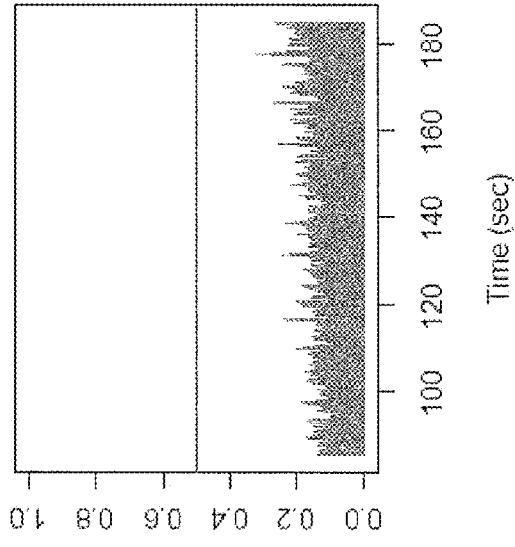
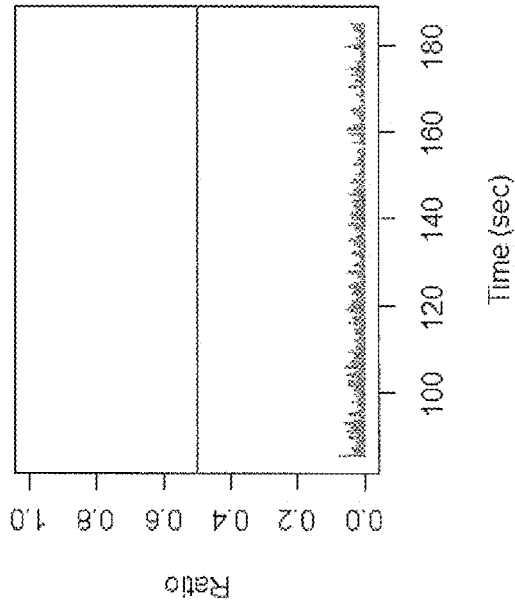

FIG. 13
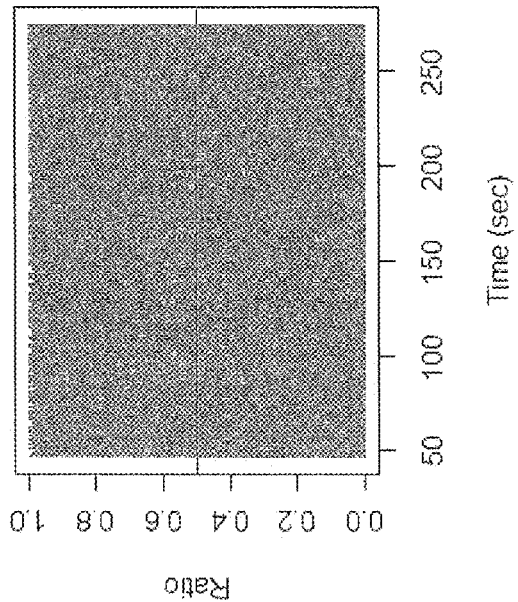
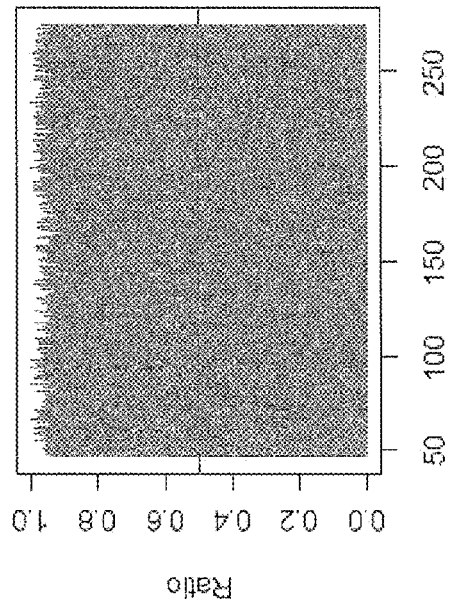

FIG. 16
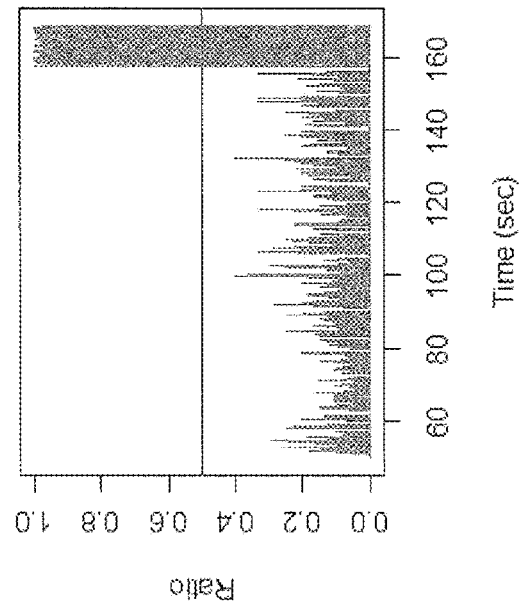
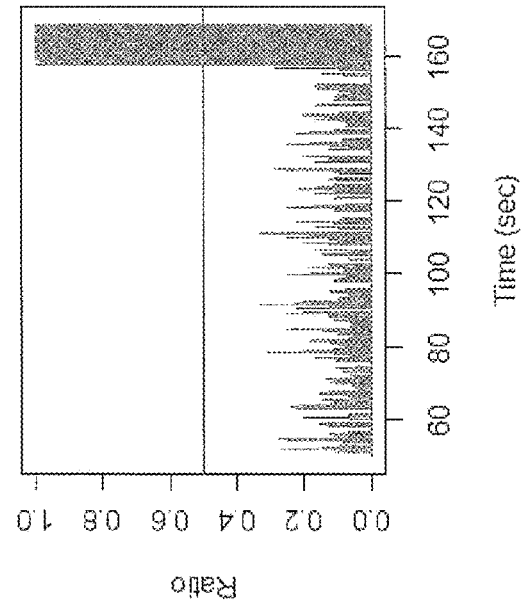

FINE PARTICLE MEASUREMENT DEVICE, AND LAMINAR FLOW MONITORING METHOD AND FINE PARTICLE ANALYSIS METHOD IN FINE PARTICLE MEASUREMENT DEVICE

CROSS REFERENCE TO RELATED APPLICATIONS

This application claims the benefit under 35 U.S.C. §371 as a U.S. National Stage Entry of International Application No. PCT/JP2013/065586, filed in the Japanese Patent Office as a Receiving Office on Jun. 5, 2013, which claims priority to Japanese Patent Application Number 2012-175214, filed in the Japanese Patent Office on Aug. 7, 2012, each of which is hereby incorporated by reference in its entirety.

TECHNICAL FIELD

The present technology relates to a fine particle measurement device, and a laminar flow monitoring method and a fine particle analysis method in the fine particle measurement device. More particularly, the present technology relates to a laminar flow monitoring method or the like of determining a liquid delivery state of a laminar flow in a flow passage formed in a flow cell, a microchip, or the like and detecting liquid delivery abnormality in a fine particle measurement device.

BACKGROUND ART

There are known fine particle measurement devices that form laminar flows containing fine particles in flow passages formed in flow cells, microchips, or the like and radiate light to the fine particles in the laminar flows to detect fluorescence and scattered light produced from the fine particles. For example, flow cytometers can measure and analyze optical characteristics of fine particles such as cells, beads, and the like based on the intensity or spectrum of detected fluorescence or scattered light.

In fine particle measurement devices, laminar flows are formed in substantially the middles of flow passages so that fine particles are circulated. Examples of the mechanism include a method of forming a sheath flow and focusing a liquid containing fine particles on the middle of a flow passage, an acoustic focusing method of aggregating fine particles on the middle of a flow passage with the energy of a sound, and a combination method thereof. However, when dust or bubbles are mixed in a flow passage, disturbance occurs in a laminar flow, a variation in the circulation positions of individual fine particles in the flow passage occurs, accurate measurement is not performed, and thus a problem occurs in reliability of data in some cases. Further, noise occurring from the dust or bubbles mixed in the flow passage deteriorates precision of data in some cases.

In relation to an embodiment of the present technology, technologies for suppressing a measurement error caused due to the variation in the circulation positions of fine particles in a flow passage are disclosed in Patent Literature 1 and Patent Literature 2. In a fluid particle analysis device disclosed in Patent Literature 1, detected light (scattered light) extracted from front scattered light, side scattered light, or rear scattered light via an optical divider is detected by a 4-split photodiode, an area CCD, and the like. Then, a position deviation from the detected position between the center of excitation light and the center of a sheath flow is detected and a position of the flow cell is adjusted so that the position deviation is within a predetermined range. Further, Patent Literature 2 discloses a technology for detecting position information regarding fine particles using a change in a deflection angle occurring in scattered light produced from the fine particles and adjusting the position of a flow cell or the focal position of the excitation light.

CITATION LIST

Patent Literature

Patent Literature 1: JP H9-166541A
Patent Literature 1: JP 2011-149822A

SUMMARY OF INVENTION

Technical Problem

According to an embodiment of the present technology, it is desirable to provide a technology for automatically determining a liquid delivery state of a laminar flow in a flow passage in order to guarantee reliability of data.

Solution to Problem

In order to solve the problem, according to the present technology, there is provided a laminar flow monitoring method in a fine particle measurement device, the method including a radiation step of radiating light to a laminar flow, a position detection step of receiving, by a detector, an S polarized component which is separated from scattered light produced from the laminar flow and to which astigmatism is given and acquiring light reception position information of the S polarized component in the detector, and a determination step of determining a state of the laminar flow based on the light reception position information.

In the position detection step, a detector of which a light reception surface may be split into a plurality of regions is used as the detector. More specifically, in the position detection step, a detector of which a light reception surface may be split into four regions, i.e., regions A, B, C, and D, in a lattice shape is used as the detector, and a difference $\Delta 1$ (A–C) between detected values of the region A and the region C not adjacent to the region A may be acquired as the light reception position information. In addition, a difference $\Delta 2$ ((A+C)–(B+D)) between a sum (A+C) of the detected values of the regions A and C and a sum (B+D) of detected values of the regions B and D may be acquired as the light reception position information. A 4-split photodiode may be used as the detector.

According to the laminar flow monitoring method according to the present technology, in the determination step, the state of the laminar flow may be determined based on the acquired difference $\Delta 1$ and/or difference $\Delta 2$. More specifically, in the determination step, the laminar flow may be determined to be abnormal when the difference $\Delta 1$ and/or the difference $\Delta 2$ deviates from a predetermined range, and the laminar flow may be determined to be normal when the difference $\Delta 1$ and/or the difference $\Delta 2$ is included within the predetermined range. More preferably, the laminar flow may be determined to be abnormal when an acquisition frequency of the difference $\Delta 1$ and/or the difference $\Delta 2$ that deviates from the predetermined range exceeds a predetermined frequency.

The laminar flow monitoring method includes a light detection step of detecting light produced from a laminar flow containing fine particles, and an analysis step of obtaining an analysis result of optical characteristics of the fine particles based on intensity information of the light acquired in the light detection step. In the analysis step, only the intensity information acquired while the laminar flow is determined to be normal is extracted and the analysis result is obtained.

Moreover, according to the present technology, there is provided a fine particle measurement device including a light radiation unit configured to radiate light to a laminar flow, a first spectroscopic element configured to separate scattered light produced from the laminar flow into an S polarized component and a P polarized component, an S polarized detector configured to receive the S polarized component, an astigmatism element arranged between the first spectroscopic element and the S polarized detector and configured to give astigmatism to the S polarized component, and a determination unit configured to receive an output from the S polarized detector, acquire light reception position information of the S polarized component, and determine a state of the laminar flow based on the light reception position information. Preferably, the astigmatism element may be a cylindrical lens.

In the S polarized detector of the fine particle measurement device, a light reception surface may be split into four regions, i.e., regions A, B, C, and D, in a lattice shape. The determination unit may acquire a difference $\Delta 1$ (A–C) between detected values of the region A and the region C not adjacent to the region A as the light reception position information. In addition, the determination unit may acquire a difference $\Delta 2$ ((A+C)−(B+D)) between a sum (A+C) of the detected values of the regions A and C and a sum (B+D) of detected values of the regions B and D as the light reception position information.

According to the fine particle measurement device according to the present technology, the determination unit may determine the state of the laminar flow based on the acquired difference $\Delta 1$ and/or difference $\Delta 2$. More specifically, the determination unit may determine the laminar flow to be abnormal when the difference $\Delta 1$ and/or the difference $\Delta 2$ deviates from a predetermined range, and determine the laminar flow to be normal when the difference $\Delta 1$ and/or the difference $\Delta 2$ is included within the predetermined range.

Preferably, the fine particle measurement device according to the present technology further includes an output unit. Information regarding the difference $\Delta 1$ and/or the difference $\Delta 2$ may be displayed in an image form on the output unit. In addition, abnormal determination of the laminar flow by the determination unit may be presented by the output unit, and the fine particle measurement device may be automatically stopped when the determination unit determines the laminar flow to be abnormal, preferably.

According to the present technology, the is provided the fine particle measurement device further including a second spectroscopic element configured to separate light produced from the laminar flow into the scattered light and fluorescence, a P polarized light detector configured to detect the P polarized component, and a fluorescence detector configured to detect the fluorescence. In addition, according to the present technology, there is provided the fine particle measurement device further including a third spectroscopic element configured to separate the fluorescence. In the fluorescence detector, a plurality of independent light-receiving elements that detect the fluorescence separated by the third spectroscopic element may be arranged so that fine particle measurement device may be configured as a spectral type fine particle measurement device.

In the present technology, the "fine particles" include biologically-relevant fine particles such as cells, microorganisms, and liposomes or synthetic particles such as latex particles, gel particles, and industrial particles.

The biologically-relevant fine particles include chromosomes, liposomes, mitochondria, and organelles constituting various cells. The cells include animal cells (such as blood cells) and plant cells. The microorganisms include bacteria such as *Escherichia coli*, viruses such as tobacco mosaic viruses, and fungi such as yeast. Further, the biologically-relevant fine particles can also include biologically-relevant macromolecules such as nucleic acids, proteins, and complexes thereof. In addition, the industrial particles, for example, may be organic or inorganic polymeric materials, or metals. The organic polymeric materials include polystyrene, styrene-divinylbenzene, polymethyl methacrylate, and the like. The inorganic polymeric materials include glass, silica, magnetic materials, and the like. The metals include colloidal gold, aluminum, and the like. In general, shapes of these fine particles are commonly spherical, but may be non-spherical. In addition, a size, mass, and the like are not particularly limited.

Advantageous Effects of Invention

According to an embodiment of the present technology, there is provided a technology for automatically determining a liquid delivery state of a laminar flow in a flow passage in order to guarantee reliability of data.

BRIEF DESCRIPTION OF DRAWINGS

FIG. 6 is a graph exemplifying a calculation straight line for calculating position information regarding the fine particle P in each of the Z-axis direction and the X-axis direction in units of micrometers from the difference $\Delta 1$ and the difference $\Delta 2$.

FIG. 9 is a graph plotting the circulation positions of the fine particles P over a given time.

FIG. 12 is a graph illustrating a temporal change of a ratio of the fine particles P of which the circulation positions deviate from the origin by a given range.

FIG. 13 is a graph illustrating a temporal change of a ratio of the fine particles P of which the circulation positions deviate from the origin by a given range.

FIG. 16 is a graph illustrating a temporal change of a ratio of the fine particles P of which the circulation positions deviate from the origin by a given range.

DESCRIPTION OF EMBODIMENTS

Hereinafter, preferred modes for carrying out the present technology will be described with reference to the drawings. Embodiments to be described below are examples of representative embodiments of the present technology and the scope of the present technology is not construed narrowly due to the embodiments. The description will be made in the following order.

Figure 1:
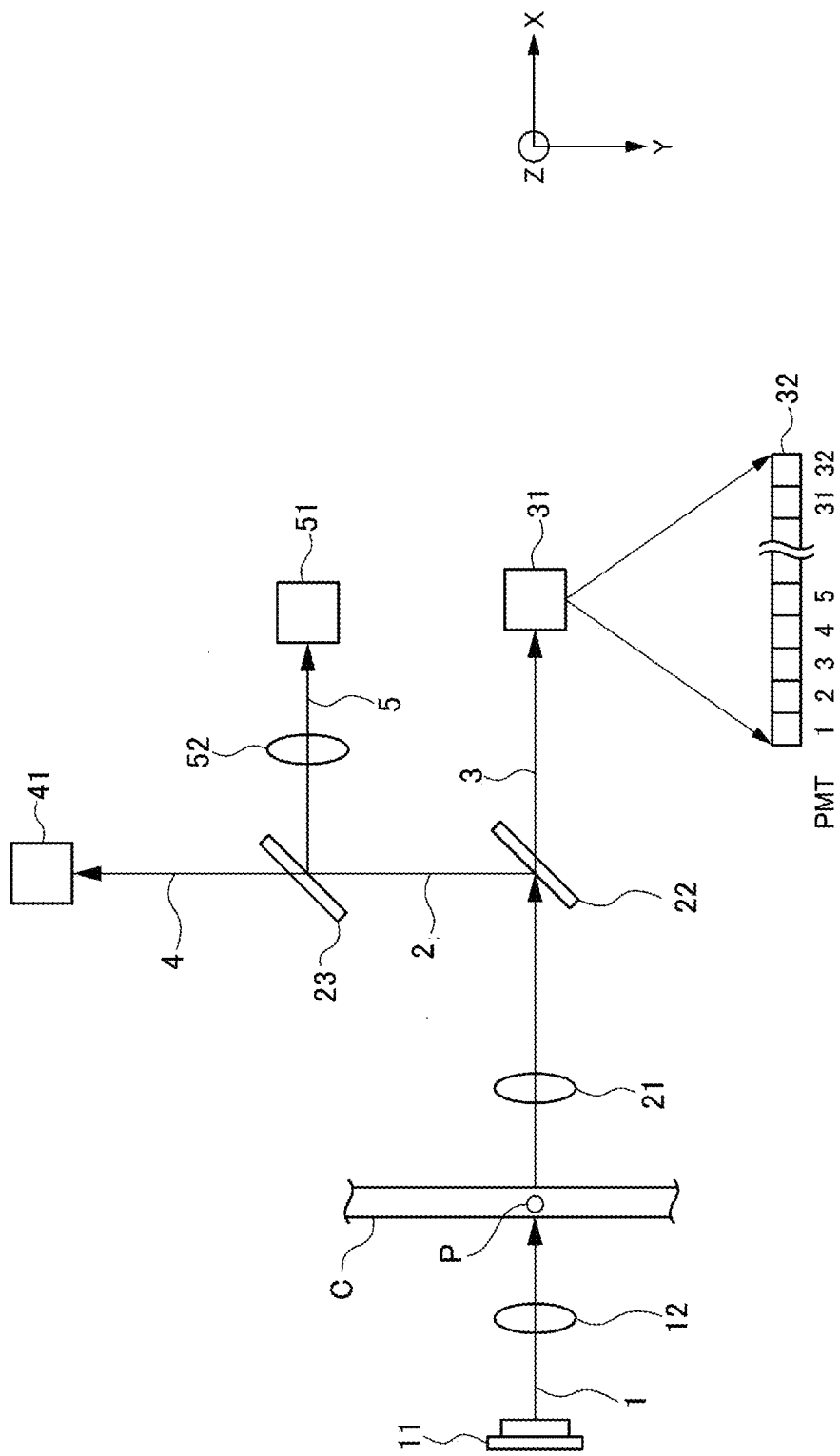
FIG. 1 is diagram for describing the configuration of a measurement unit of a fine particle measurement device according to an embodiment of the present technology.

1. Configuration of fine particle measurement device
  (1) Measurement unit
  (1-1) Light radiation unit
  (1-2) Light detection unit
  (2) Determination unit
  (3) Output unit
2. Laminar flow monitoring process in fine particle measurement device
  (1) Light reception position detecting step
  (2) Determining step
  (3) Operation in time of abnormality detection
3. Modification examples
  (1) Light detection unit
  (2) S polarized detector
4. Laminar flow monitoring method and laminar flow monitoring program 1. Configuration of Fine Particle Measurement Device (1) Measurement Unit FIG. 1 is diagram for describing the configuration of a measurement unit of a fine particle measurement device according to an embodiment of the present technology. The fine particle measurement device according to the embodiment of the present technology is roughly configured to include an illustrated measurement unit and a determination unit (not illustrated). In the fine particle measurement device, a control unit including a CPU may be installed to control the measurement unit and the determination unit. The measurement unit includes a light radiation unit that radiates excitation light 1 to a laminar flow circulating a flow passage C and a light detection unit that detects scattered light 2 and fluorescence 3 produced from the laminar flow. A reference sign P in the drawing indicates fine particles contained in the laminar flow.

(1-1) Light Radiation Unit

The light radiation unit is configured to include a light source 11 that emits the excitation light 1 and an objective lens 12 that condenses the excitation light 1 to the laminar flow circulating the flow passage C formed in a flow cell, a microchip, and the like. The light source 11 is appropriately selected from a laser diode, a second harmonic generation (SHG) laser, a solid-state laser, a gas laser, a high-luminance light emitting diode (LED), and the like according to a measurement purpose. In the light radiation unit, optical elements may be disposed in addition to the light source 11 and the objective lens 12, as necessary.

(1-2) Light Detection Unit

The light detection unit is configured to include a condensing lens 21, spectroscopic elements 22, 23, and 31, a fluorescence detector 32, a P polarized light detector 41, an S polarized light detector 51, and an astigmatism element 52.

The condensing lens 21 condenses the scattered light 2 and the fluorescence 3 produced from the laminar flow and/or the fine particles P in the laminar flow to which the excitation light 1 is radiated. The scattered light 2 may be any of various kinds of scattered light such as front scattered light, side scattered light, Rayleigh scattered light, and Mie scattered light. The fluorescence 3 may be fluorescence produced from the fine particles P or fluorescence produced from a fluorescent material with which the fine particles P are labeled.

The spectroscopic element 22 separates the scattered light 2 and the fluorescence 3 condensed by the condensing lens 21. In the spectroscopic element 22, a dichroic mirror that reflects only light with specific wavelengths and transmits light with other wavelength components is used. In the fine particle measurement device according to the embodiment, a dichroic mirror that reflects the scattered light 2 and transmits the fluorescence 3 is used.

The spectroscopic element 31 is considered to be a prism, a grating mirror, or the like and further separates the fluorescence 3 separated by the spectroscopic element 22 to project the fluorescence 3 to the fluorescence detector 32. The fluorescence detector 32 detects the fluorescence 3 separated by the spectroscopic element 22. In the fluorescence detector 32, a plurality of independent light-receiving elements are arranged and each light-receiving element detects light with a wavelength band split from the fluorescence 3 and projected from the spectroscopic element 31. In the fine particle measurement device according to the embodiment, a PMT array in which photo multiplier tubes (PMTs) of 32 channels are arranged in a 1-dimensional manner as the light-receiving elements is used as the fluorescence detector 32. The fluorescence detector 32 converts intensity information of the detected fluorescence 3 into an electric signal and outputs the electric signal to a calculation unit. The calculation unit analyzes the fluorescent characteristics of the fine particles P based on the electric signal. Further, a photodiode array or a 2-dimensional light-receiving element such as a CCD and a CMOS may be used as the fluorescence detector 32.

By combining the spectroscopic element 31 and using a light-receiving element array or a 2-dimensional light-receiving element in the fluorescence detector 32, it is possible to acquire the fluorescence 3 produced from the fine particles P as a spectrum.

The P polarized light detector 41 detects a P polarized component 4 included in the scattered light 2 separated by the spectroscopic element 22. In the P polarized light detector 41, for example, a photodiode (PD), a charge coupled device (CCD), or a photo-multiplier tube (PMT) can be used. The P polarized light detector 41 converts intensity information of the detected P polarized component 4 into an electric signal and outputs the electric signal to the calculation unit. The calculation unit analyzes the scattered light characteristics of the fine particles P based on the electric signal. The sizes, inner structures, and the like of the fine particles P can be analyzed from the intensity information of the P polarized component 4.

The spectroscopic element 23 separates incident non-polarized light into two pieces of polarized light of which vibration directions are perpendicular, i.e., separates the scattered light 2 separated by the spectroscopic element 22 into the P polarized component 4 and an S polarized component 5. Specifically, the spectroscopic element 23 transmits the P polarized component 4 in the incident scattered light 2 and reflects the S polarized component 5.

Figure 2:
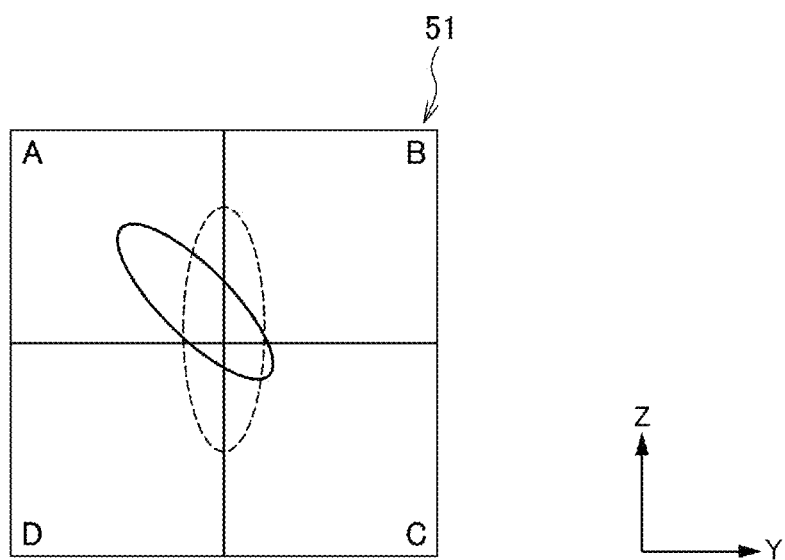
FIG. 2 is a diagram for describing the configuration of a light reception surface of an S polarized light detector 51.

The S polarized light detector 51 detects the S polarized component 5 separated by the spectroscopic element 23 and a light reception surface thereof is split into a plurality of regions. In the fine particle measurement device according to the embodiment, as illustrated in FIG. 2, a 4-split photodiode in which the light reception surface is split into four regions, i.e., regions A, B, C, and D, in a lattice shape is used.

The astigmatism element 52 is a cylindrical lens arranged between the spectroscopic element 23 and the S polarized light detector 51 and gives astigmatism to the S polarized component 5 transmitted toward the S polarized light detector 51. A signal detected by the S polarized light detector 51 is output to the determination unit. The determination unit receives the output and acquires information (light reception position information) regarding a light reception position of the S polarized component 5 in which the astigmatism occurs on the light reception surface of the S polarized light detector 51. The light reception position (image formation pattern) of the S polarized component 5 on the light reception surface of the S polarized light detector 51 will be described in detail later.

(2) Determination Unit

The determination unit performs a process of determining the state of a laminar flow circulating the flow passage C based on the light reception position information of the S polarized component 5 on the light reception surface of the S polarized light detector 51. The determination unit is configured to include a hard disk storing an OS and a program executing this process, a CPU, and a memory.

(3) Output Unit

The fine particle measurement device according to an embodiment of the present technology includes an output unit that presents the state of the laminar flow and the determination result to a user. A known output device of the related art, such as a display, a printer, or a speaker, is used as the output unit.

2. Laminar Flow Monitoring Method in Fine Particle Measurement Device

Next, a process by which the determination unit determines a liquid delivery state of the laminar flow will be described.

(1) Light Reception Position Detecting Step

The determination unit first acquires differences in a detected value between the plurality of regions formed in the light reception surface of the S polarized light detector 51 based on the light reception position information of the S polarized component 5 on the light reception surface of the S polarized light detector 51. Specifically, the determination unit acquires a difference $\Delta 1$ (A–C) and a difference $\Delta 2$ ((A+C)–(B+D)) between the detected values in the regions A, B, C, and D of the 4-split photodiode illustrated in FIG. 2.

Figure 3:
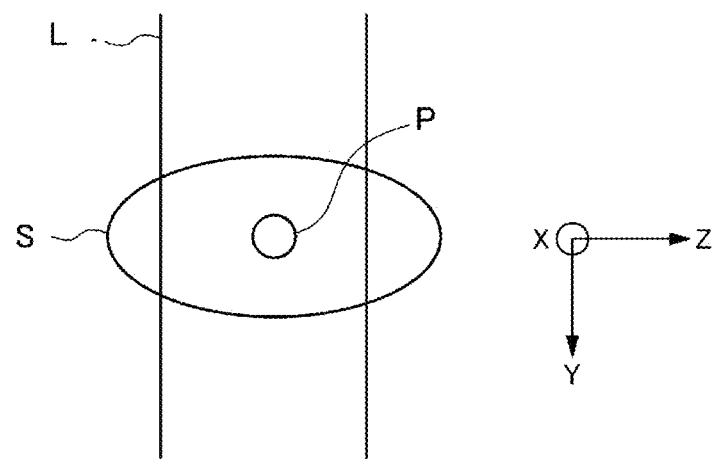
FIG. 3 is a diagram for describing a laminar flow L circulating a flow passage C and a laser spot S of excitation light 1 radiated to the laminar flow L.

FIG. 3 illustrates the laminar flow L circulating the flow passage C, the fine particle P in the laminar flow L, and a laser spot S of the excitation light 1 radiated to the laminar flow L. In the drawing, a radiation direction of the excitation light 1 to the laminar flow L is assumed to be an X-axis direction and a liquid delivery direction of the laminar flow L is assumed to be a Y-axis direction. A direction perpendicular to the X-axis direction and the Y-axis direction is assumed to be a Z-axis direction. The present inventors have found that position information of the fine particle P in the Z-axis direction can be acquired from the foregoing difference $\Delta 1$ (A–C) and position information of the fine particle P in the X-axis direction can be acquired from the foregoing difference $\Delta 2$ ((A+C)–(B+D)).

When the fine particle P circulates the central position of the laser spot S in FIG. 3 and a focal position of the excitation light 1 matches a circulation position of the fine particle P, the image formation pattern (light reception position) of the S polarized component 5, to which the astigmatism is given by the astigmatism element 52, on the light reception surface of the S polarized light detector 51 becomes an image indicated by a central dotted line in FIG. 2. On the other hand, when the fine particle P circulates a peripheral position that deviates from the center of the laser spot S and the focal position of the excitation light 1 does not match the circulation position of the fine particle P, the image formation pattern becomes, for example, an image indicated by a solid line in FIG. 2. That is, the image formation pattern of the S polarized component 5 is changed to correspond to the circulation position of the fine particle P and ratios at which the S polarized component 5 is projected to the regions A to D are changed to correspond to the circulation position of the fine particle P. Therefore, the circulation position of the fine particle P is reflected directly to patterns of the detected values of the S polarized component 5 in the regions A to D.

Figure 4:
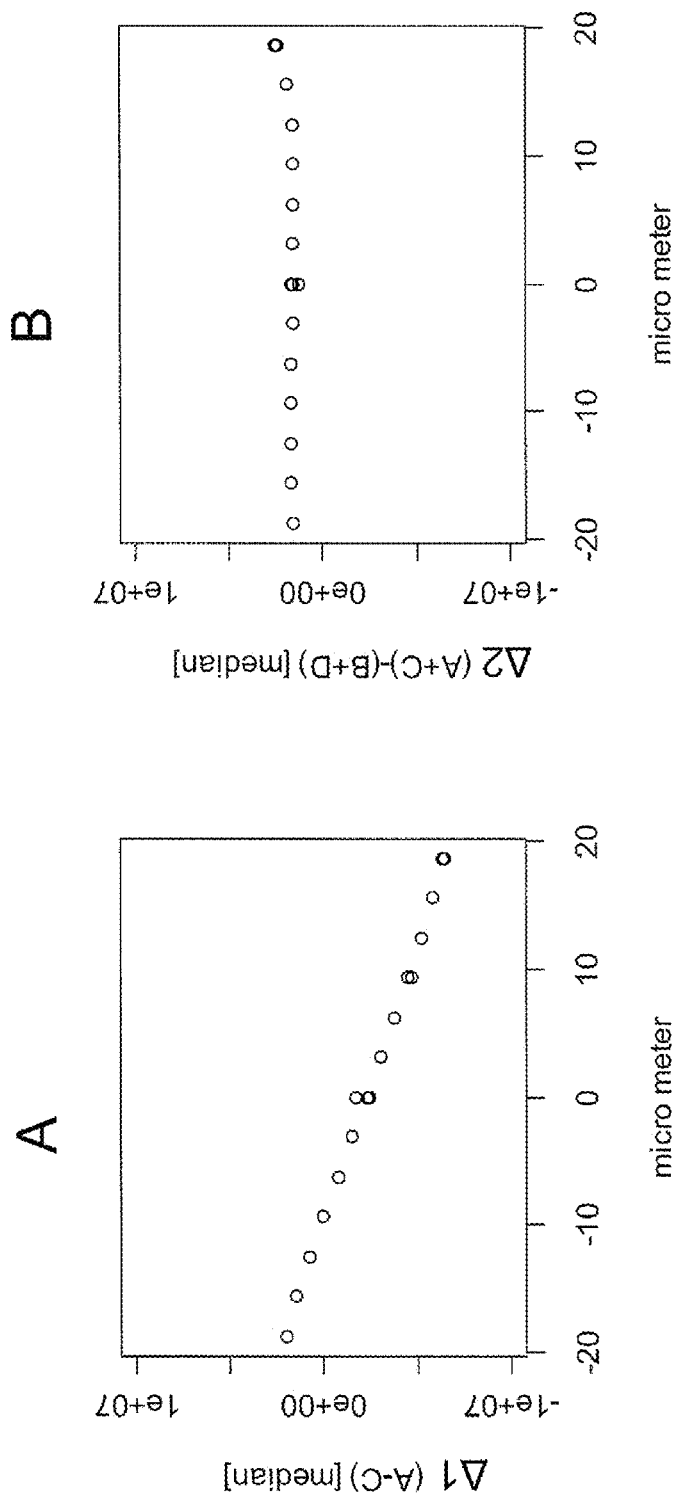
FIG. 4 is a graph exemplifying a change in each of a difference $\Delta 1$ and a difference $\Delta 2$ when the circulation position of the fine particle P is moved in a Z-axis direction.

A change in the difference $\Delta 1$ (A–C) and a change in the difference $\Delta 2$ ((A+C)–(B+D)) when a flow cell in which the fine particle P is circulated is moved in the Z-axis direction by a stepping motor are shown in FIG. 4. The vertical axis represents an average value of each of the difference $\Delta 1$ (A–C) and the difference $\Delta 2$ ((A+C)–(B+D)). The horizontal axis represents a movement amount of the stepping motor in units of micrometers. In the movement amount of the stepping motor, an actual length (in units of micrometers) can be calculated from the number of pulses (a driving amount).

The origin (zero), which is a movement start position of the flow cell, may be any position, but may be a position at which particles can be measured most appropriately under the condition in which the laminar flow is formed normally. For example, a position at which the intensity of the scattered light or the fluorescence detected from the individual fine particle P is the highest can be set or a position at which a CV value of the intensity of the scattered light or the fluorescence is the lowest can be set.

As illustrated in FIG. 4, only the difference $\Delta 1$ (A–C) is changed in relation with the movement amount in the Z-axis direction. From this, it can be understood that the position information of the fine particle P in the Z-axis direction can be obtained from the difference $\Delta 1$. It can also be confirmed that the movement amount in the Z-axis direction and the difference $\Delta 1$ have a linear relation. FIG. 6A illustrates a straight line for calculating the position information of the fine particle P in the Z-axis direction in units of micrometers from the difference $\Delta 1$.

Figure 5:
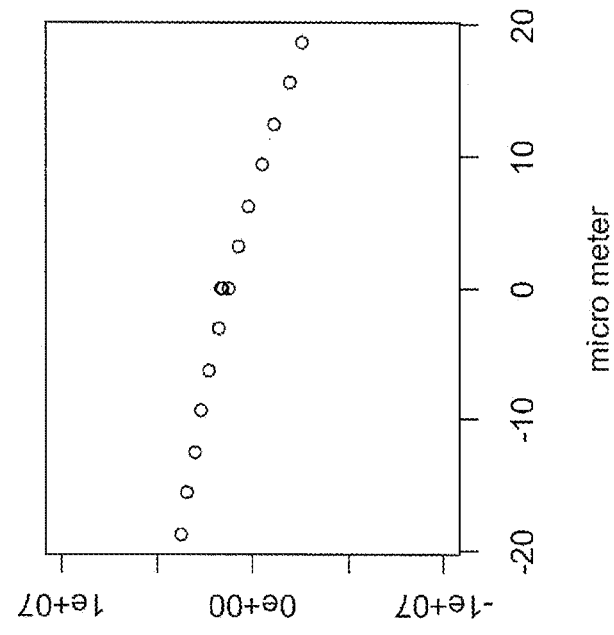
FIG. 5 is a graph exemplifying the change in each of the difference $\Delta 1$ and the difference $\Delta 2$ when the circulation position of the fine particle P is moved in an X-axis direction.

A change in the difference $\Delta 1$ (A–C) and a change in the difference $\Delta 2$ ((A+C)–(B+D)) when a flow cell in which the fine particle P is circulated is moved in the X-axis direction by the stepping motor are shown in FIG. 5. Only the difference $\Delta 2$ is changed in relation with the movement amount in the X-axis direction. From this, it can be understood that the position information of the fine particle P in the X-axis direction can be obtained from the difference $\Delta 2$. It can also be confirmed that the movement amount in the X-axis direction and the difference $\Delta 2$ have a linear relation. FIG. 6B illustrates a straight line for calculating the position information of the fine particle P in the X-axis direction in units of micrometers from the difference $\Delta 2$.

As described above, a variation in the circulation position of the fine particle P occurs due to disturbance of the laminar flow L. Accordingly, the variation in the circulation position of the fine particle P is the variation in which the liquid delivery state of the laminar flow L is reflected. That is, the position information of the fine particle P obtainable from the difference Δ1 (A−C) and the difference Δ2 ((A+C)−(B+D)) can be used as information indicating the liquid delivery state of the laminar flow L.

Various calculation processes for the differences in the detected values and the position information of the fine particle P, as described above, can be performed by a unit including a CPU capable of performing such calculation processes. For example, the measurement unit and the determination unit described above can be exemplified as the unit including the CPU capable of performing the calculation processes.

This will be described specifically with reference to FIGS. 7 to 11. The drawings are graphs obtained by calculating the difference Δ1 and the difference Δ2 from the detected values which are equal to or greater than a given threshold value among the detected values of the S polarized component 5 produced from the laminar flow L and calculating and plotting the circulation positions of the fine particles P over a given time. The circulation positions from the difference Δ1 and the difference Δ2 are calculated using the calculated straight line illustrated in FIG. 6. In the drawings A and B, the horizontal axis represents time and the vertical axis represents the position information in the Z-axis direction or the X-axis direction in units of micrometers. In the drawing C, the horizontal axis represents the Z-axis direction and the vertical axis represents the position information in the X-axis direction in units of micrometers. In each drawing, the color of the plot represents the density (population) of the fine particles.

Figure 7:
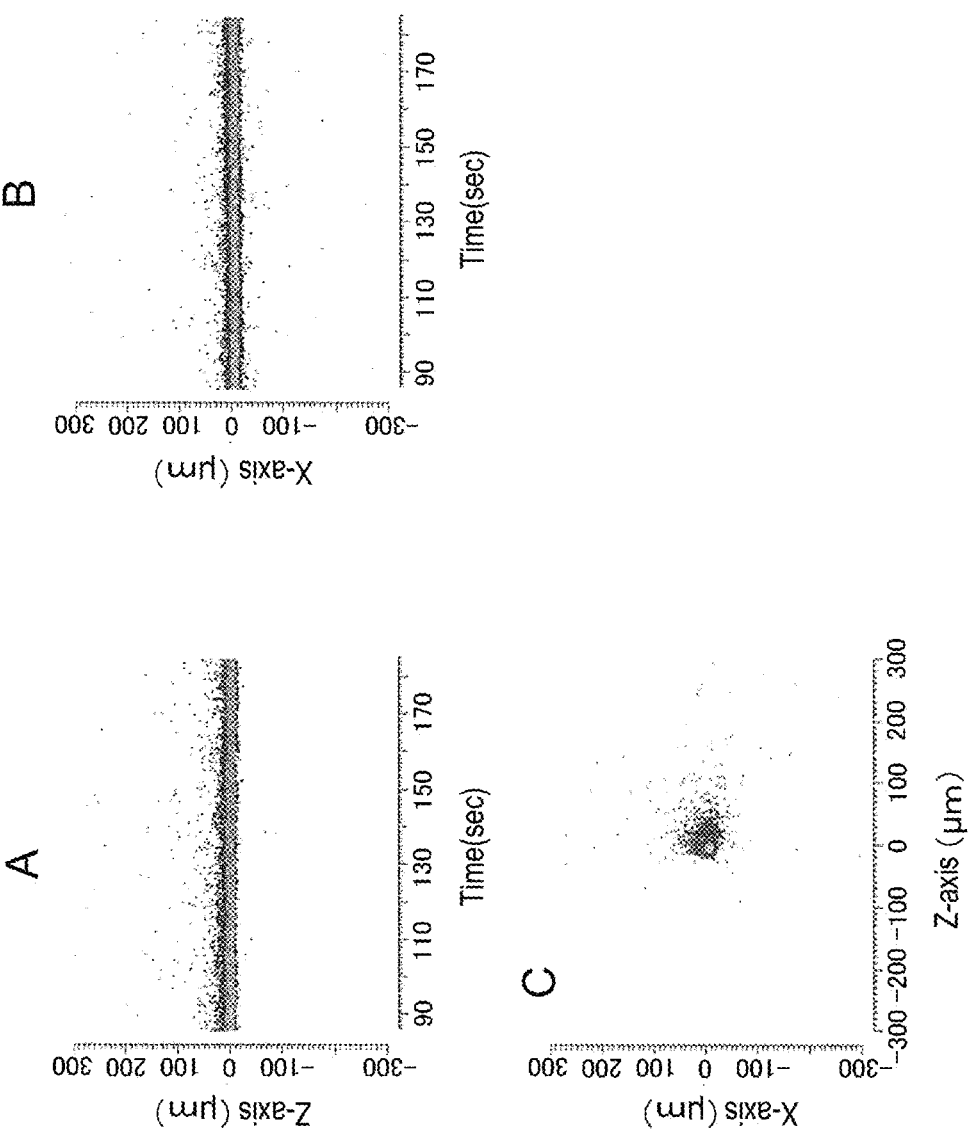
FIG. 7 is a graph plotting the circulation positions of the fine particles P over a given time.

FIG. 7 illustrates an example in which the appropriate laminar flow L stabilized from the beginning to the end of the measurement is formed. From the drawing C, it can be understood that the fine particles P flow to be concentrated in the substantial vicinity of the origin. Further, from the drawing A and the drawing B, it can be understood that the fine particles P are stabilized from the beginning to the end of the measurement and flow in the vicinity of the origin.

Figure 8:
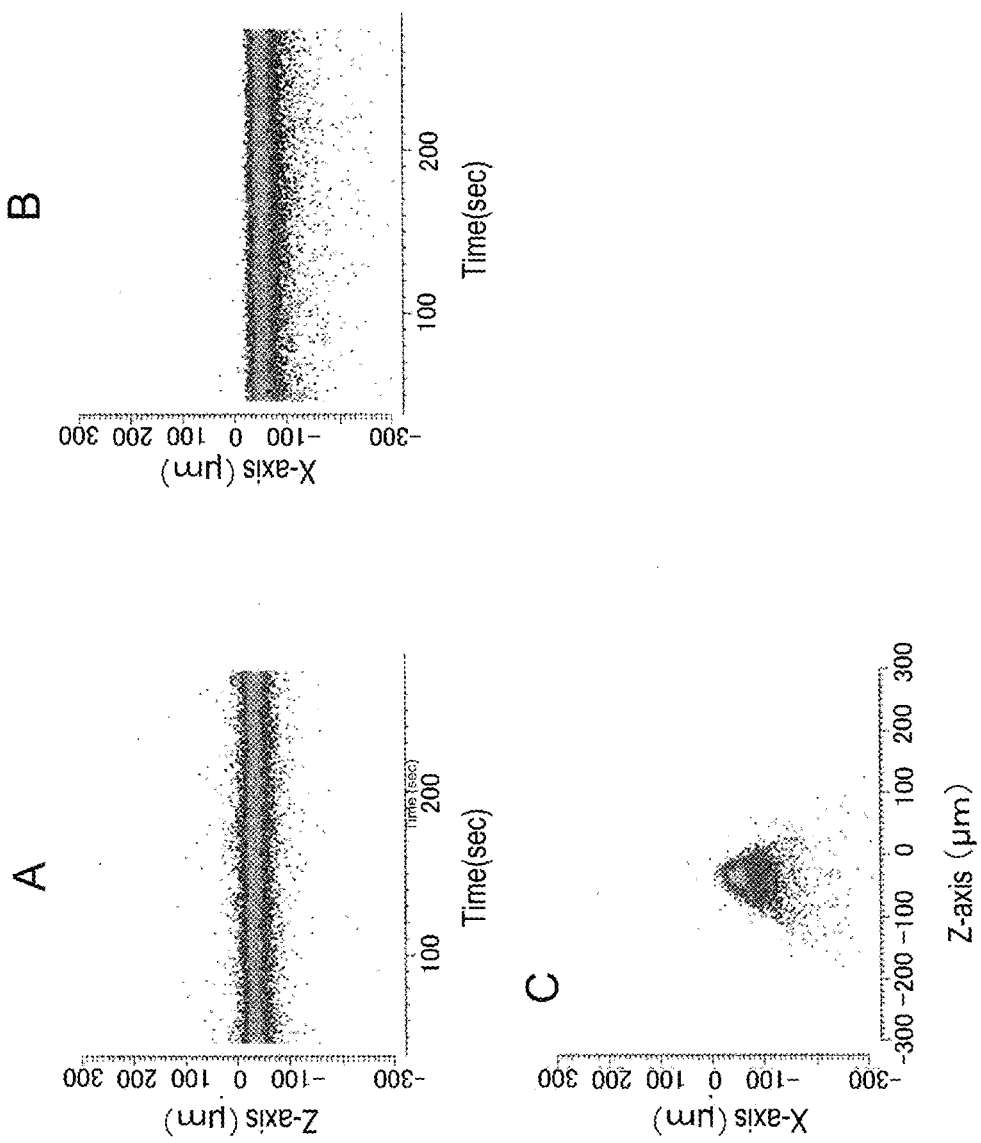
FIG. 8 is a graph plotting the circulation positions of the fine particles P over a given time.

FIGS. 8 and 9 illustrate examples in which the laminar flow L is disturbed. In FIGS. 8A and 8B, a constant tendency is shown with respect to the time axis, but the circulation positions of the fine particles P are disturbed in the negative direction of the X-axis. In FIG. 8C, it can be understood that the circulation positions of the fine particles P spread in the X-axis direction. In FIGS. 9A and 9B, a constant tendency is shown with respect to the time axis, but the circulation positions of the fine particles P are disturbed in the positive and negative directions of the Z-axis. In FIG. 9C, it can be understood that the circulation positions of the fine particles P spread in the positive and negative directions of the Z-axis. The deviation of the circulation positions of the fine particles P occurs when foreign matters such as dust or bubbles are attached to the inner wall of the flow passage circulating the laminar flow L and stable liquid delivery is inhibited. Further, the circulation positions deviate in some cases since a liquid delivery pressure of the laminar flow L becomes an inappropriate pressure due to a setting error or breakdown (air leakage) of the device.

Figure 10:
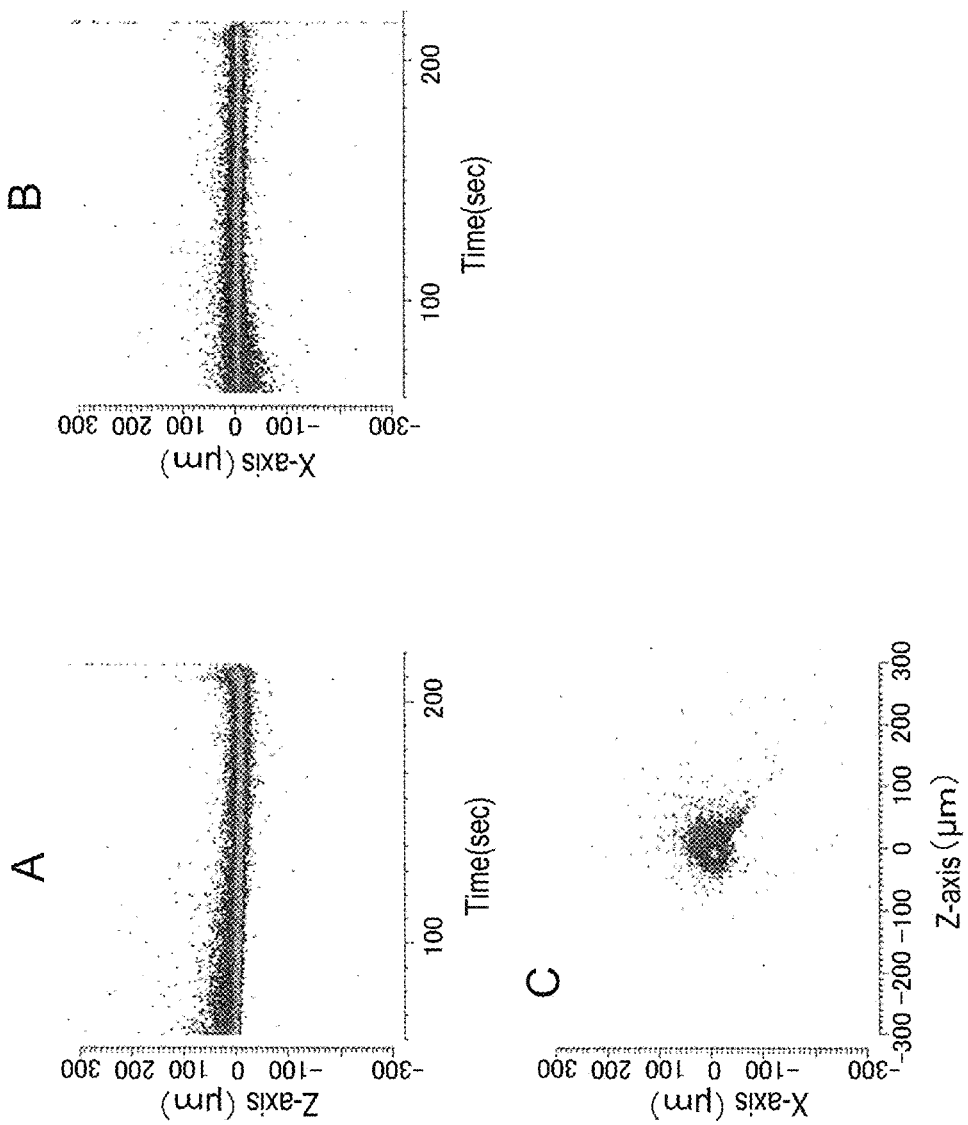
FIG. 10 is a graph plotting the circulation positions of the fine particles P over a given time.
Figure 11:
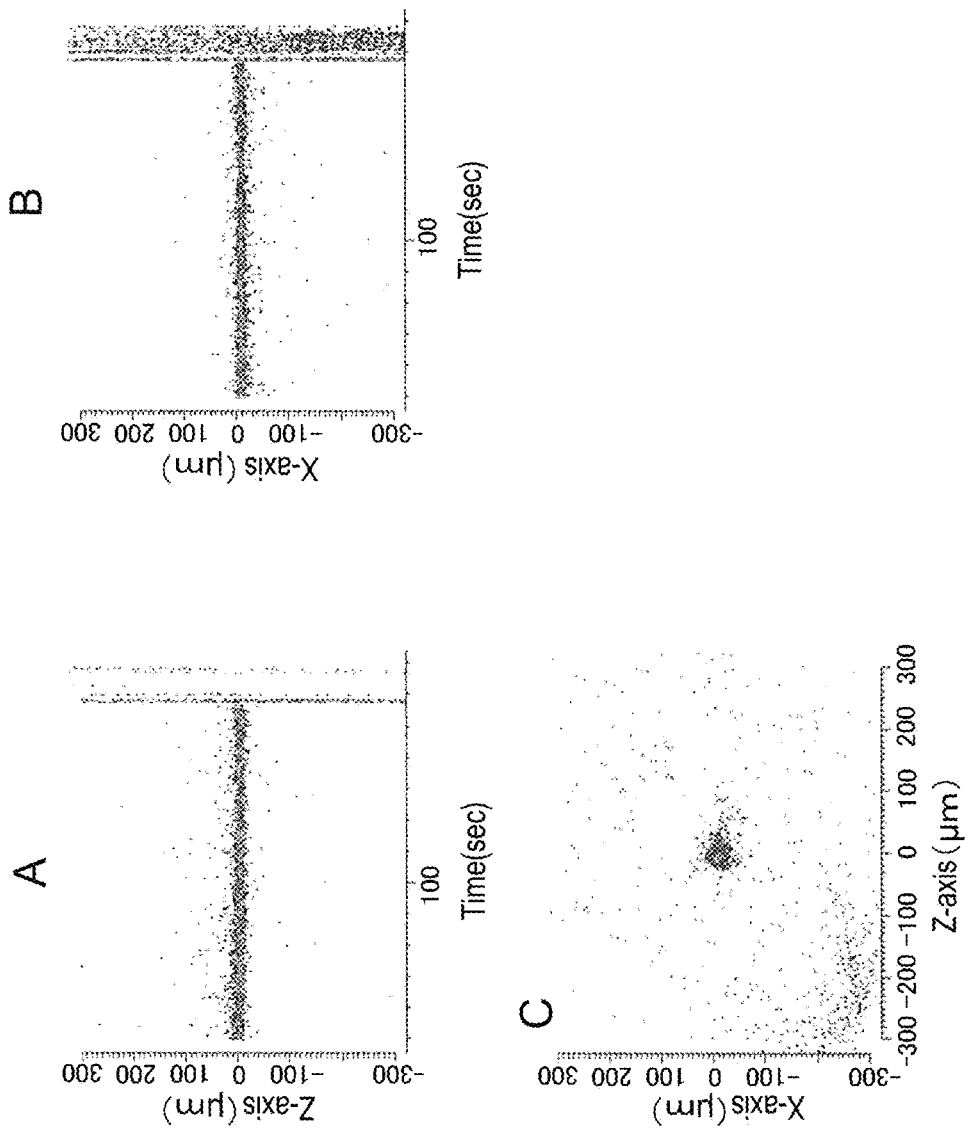
FIG. 11 is a graph plotting the circulation positions of the fine particles P over a given time.
Figure 14:
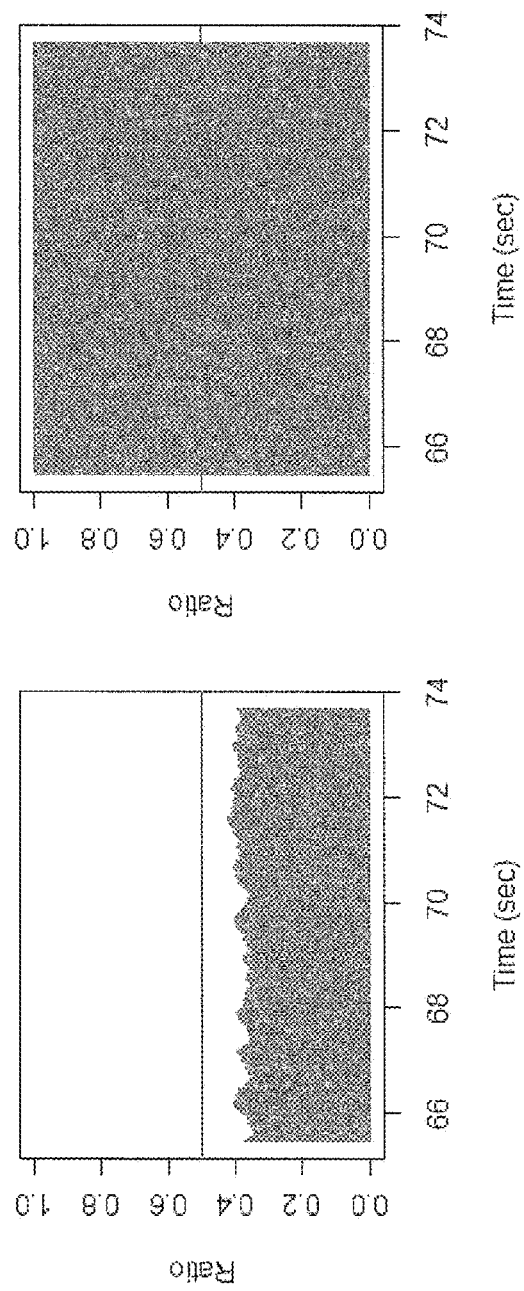
FIG. 14 is a graph illustrating a temporal change of a ratio of the fine particles P of which the circulation positions deviate from the origin by a given range.

FIGS. 10 and 11 illustrate examples in which the disturbance of the laminar flow L occurs during measurement. In FIGS. 10 and 11, the circulation positions of the fine particles P diffuse in a broad range in the Z-axis direction and the X-axis direction immediately before the end of the measurement. The diffusion of the circulation positions occurs when air infiltrates the flow passage in which the laminar flow L is circulated and becomes bubbles, and results from detection of the scattered light produced from the surfaces of the bubbles propagated and flowing in the entire flow passage. The mixing of the bubbles into the flow passage occurs in some cases due to interruption of supply of a liquid (a sheath liquid or a sample liquid containing the fine particles P) forming the laminar flow L to the flow passage.

(2) Determining Step

As described with reference to FIGS. 7 to 11, the liquid delivery state of the laminar flow L can be determined based on the difference Δ1 (A−C) and the difference Δ2 ((A+C)−(B+D)). While the disturbance of the laminar flow L occurs, as illustrated in FIGS. 8 and 9, the optical characteristics of the fine particles P are considered not to be appropriately measured. For this reason, previously acquired data is preferably not used in the analysis. Further, data acquired after the mixing of the bubbles into the flow passage occurs, as described with reference to FIGS. 10 and 11, is preferably not used in the analysis either since the data is not normal data.

When the difference Δ1 (A−C) and the difference Δ2 ((A+C)−(B+D)) calculated from the detected values of the S polarized component 5 from the laminar flow L spread or diffuse beyond a predetermined range (see FIGS. 8 to 11), the determination unit determines that the liquid delivery state of the laminar flow L is abnormal. For example, when a ratio of the number of detected events, for which the difference Δ1 (A−C) and the difference Δ2 ((A+C)−(B+D)) exceed a predetermined range, to the number of previously detected events reaches a predetermined value, the determination unit performs abnormality determination. Conversely, when the difference Δ1 (A−C) and the difference Δ2 ((A+C)−(B+D)) do not exceed the predetermined value, the determination units determines that the liquid delivery state of the laminar flow L is normal.

A process for the abnormality determination based on the ratio of the number of detected events will be described specifically with reference to FIGS. 12 to 16. In FIGS. 12 to 16, ratios of the fine particles P of which the circulation positions deviate from a given range are respectively calculated from the graphs plotting the circulation positions of the fine particles P illustrated in FIGS. 7 to 11 over a given time, and time is graphed on the horizontal axis. In each drawing, the particles that deviate from a range of the origin ±20 micrometers are plotted as 1, the particles flowing within the range are plotted as 0 on the vertical axis, and the results are smoothed using a kernel smoothing method on the horizontal axis representing a measured time. The drawing A illustrates the result in the Z-axis direction and the drawing B illustrates the result in the X-axis direction. Averaging is not a mandatory process and various methods such as moving average, index moving average, and spline smoothing may be used in addition to the kernel smoothing method. When the kernel smoothing method, the moving average method, or the like is applied to the plot, the horizontal axis of the plot is not limited to time, but may represent the counted number of detected particles or the like.

Figure 15:
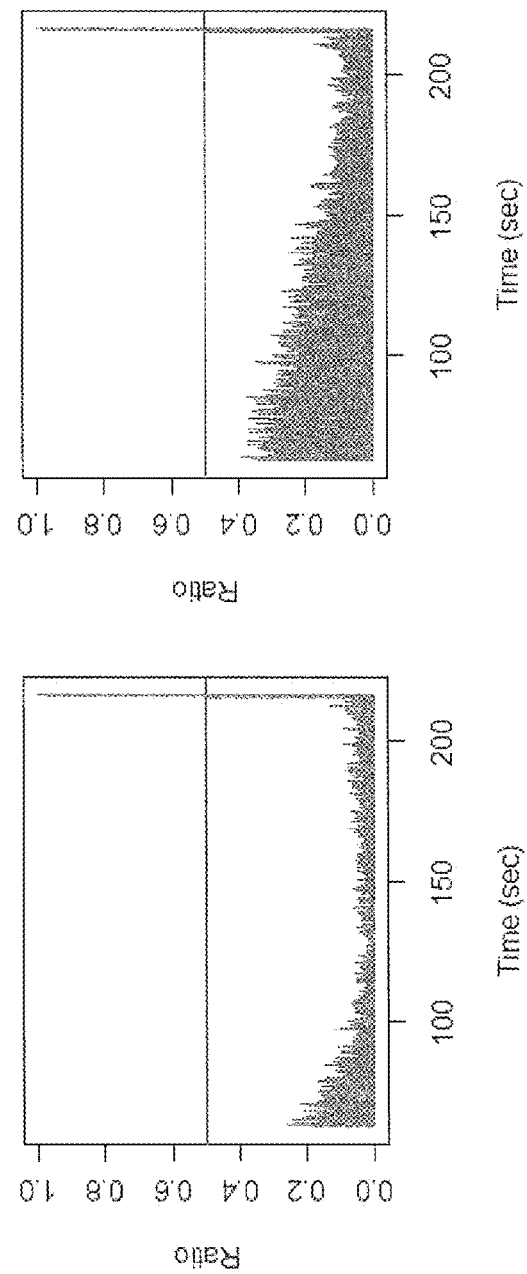
FIG. 15 is a graph illustrating a temporal change of a ratio of the fine particles P of which the circulation positions deviate from the origin by a given range.

In the example of FIG. 12 in which the appropriate laminar flow L stabilized from the beginning to the end of the measurement is formed, the ratio of the fine particles P that deviate from the range of the origin ±20 micrometers is suppressed to be low in both of the Z-axis direction and the X-axis direction. Conversely, in the examples of FIGS. 13 and 14 in which the laminar flow L is disturbed, the ratios have large values. In the examples of FIGS. 15 and 16 in which the mixing of the bubbles into the flow passage occurs, a steep increase in the ratios can be confirmed immediately before the end of the measurement. Accordingly, the ratios can be said to be indexes of the stabilization of the liquid delivery state of the laminar flow. For example, when the upper limit of the ratio is set to 0.5 and the ratio exceeds the upper limit, the liquid delivery state of the laminar flow L can be determined to be abnormal.

In the graphs in which the circulation positions of the fine particles P illustrated in FIGS. 10 and 11 are plotted for a given time, there is a probability of linearity of the difference Δ1 or the difference Δ2 illustrated in FIG. 6 and the position information of the fine particles P not being maintained in the plots in which the fine particles P are excessively distant (for example, 100 micrometers) from the origin. In this case, however, by setting a constant range condition as in the foregoing example (the origin ±20 micrometers), the liquid delivery abnormality can be effectively determined. Here, the range condition of the origin ±20 micrometers has been exemplified, but the range condition can be appropriately set according to the liquid delivery condition at the time of the measurement, the shape of the flow passage, or the like.

The graphs (see FIGS. 7 to 11) plotting the circulation positions of the fine particles P for the given time and the graphs (see FIGS. 12 to 16) showing the temporal change in the ratio of the fine particles P that deviate from the given range are useful in determining the state of the laminar flow L visually and intuitively. Accordingly, in the fine particle measurement device according to an embodiment of the present technology, the output unit is configured to display information derived from the difference Δ1 and the difference Δ2. Specifically, by allowing the output unit to display the graphs (see FIGS. 7 to 11) plotting the circulation positions of the fine particles P for the given time and the graphs (see FIGS. 12 to 16) showing the temporal change in the ratio of the fine particles P that deviate from the given range in image forms, it is also possible to indicate the liquid delivery state of the laminar flow L to the user visually in real time. The axes used in the graphs may be substituted with position information (in micrometers) calculated from the difference Δ1 and the difference Δ2, so that the values of the difference Δ1 and the difference Δ2 may be used without change. In this case, the values of the difference Δ1 and the difference Δ2 at the optimum circulation positions of the fine particles P are preferably acquired in advance and the values are preferably set to the origin (zero).

(3) Operation when Abnormality is Detected

It is preferable that the determination unit frequently determine the liquid delivery state of the laminar flow L during a device operation. When the determination unit determines that the liquid delivery state is abnormal, the determination unit performs the following process.

[Alert]

The user can confirm the liquid delivery state of the laminar flow L in real time during the measurement based on information regarding the difference Δ1 and the difference Δ2 displayed on the output unit to handle abnormality. Further, the determination unit may indicate a warning (alert) to the user through the output unit to the user. A form of the indication may be, for example, an image indication on a display, a text or graphics indication by a printer, or a sound indication by a speaker. When the alert is indicated, the user can confirm the alert and interrupt the measurement immediately, and thus waste of a sample or time can be eliminated.

When the user confirms the disturbance of the laminar flow L by the alert, the user preferably interrupts the measurement. Then, it is preferable to perform a cleaning task of removing attached foreign matters such as dust or bubbles on the inner wall of the flow passage or perform a resetting task such as adjustment of a liquid feeding pressure of the laminar flow L. After the resetting task, the waste of the sample or the time can be eliminated by resuming the measurement after the stable liquid delivery is confirmed. When the mixing of the bubbles into the flow passage is confirmed, it is desirable to interrupt the measurement and prevent bubbles from flowing in further. When many bubbles flow into the flow passage, it takes time to remove the bubbles, and thus there is a concern of resuming the measurement in spite of the fact the bubbles are incompletely removed.

[Automatic Stop]

When the liquid delivery state is determined to be abnormal, the device may automatically stopped instead of the foregoing alert or along with the alert. Thus, the waste of a sample or time can be eliminated and further flow of the bubbles in the flow passage can be prevented.

[Data Exclusion]

The determination unit may perform a process of excluding the intensity information acquired during abnormality of the liquid delivery state of the laminar flow L when the analysis result of the optical characteristics of the fine particles P is obtained based on the intensity information of the fluorescence 3 and the P polarized component 4 produced from the fine particles P. By extracting and using only the intensity information acquired at the time of normality to analyze the optical characteristics of the fine particles P, inappropriate data acquired at the time of the liquid delivery abnormality can be excluded, and thereby accurate analysis results can be obtained and reliability of the data can be improved.

As described above, the fine particle measurement device according to an embodiment of the present technology determines the liquid delivery state of the laminar flow from the light reception position information on the light reception surface of the detector of the scattered light produced from the laminar flow and automatically detects liquid delivery abnormality. In the fine particle measurement device according to an embodiment of the present technology, when the optical characteristics of the fine particles after the measurement are analyzed, it can be found whether or not inappropriate data due to the liquid delivery abnormality is included in the analysis result by confirming the liquid delivery state of the laminar flow at the time of the measurement, and thus certainty (reliability) of the analysis result can be evaluated.

When the liquid delivery abnormality of the laminar flow is detected, the fine particle measurement device according to an embodiment of the present technology gives an alert or is automatically stopped. Therefore, it is possible to eliminate the waste of a sample or time caused due to continuation of the measurement while the liquid delivery state is abnormal. Further, in the fine particle measurement device according to an embodiment of the present technology, the analysis can be performed with high precision since inappropriate data acquired at the time of liquid delivery abnormality can be excluded and the analysis result of the optical characteristics of the fine particles can be obtained.

3. Modification Examples (1) Light Detection Unit

Figure 17:
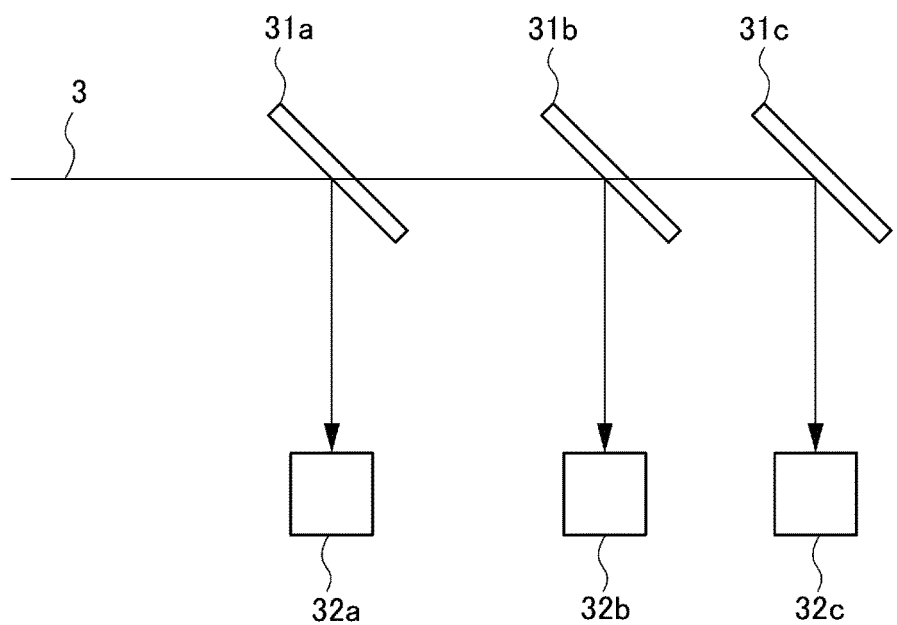
FIG. 17 is a diagram for describing the configuration of a light detection unit according to a modification example.

In the fine particle measurement device according to the above-described embodiment, the example in which the light detection unit is configured by combining the spectroscopic element 31 and the fluorescence detector 32 formed as the light-receiving element array or the 2-dimensional light-receiving element and the fluorescence 3 produced from the fine particles P is acquired as a spectrum has been described. In the fine particle measurement device according to an embodiment of the present technology, as illustrated in FIG. 17, the light detection unit may be configured to select only a desired wavelength band from the fluorescence 3 using a plurality of wavelength selection elements (here, three elements denoted by reference numerals 31a, 31b, and 31c) and detect the fluorescence using fluorescence detectors (here, three detectors denoted by reference numerals 32a, 32b, and 32c). In the wavelength selection elements 31a, 31b, and 31c, dichroic mirrors reflecting only light of a specific wavelength band and transmitting light of other wavelength bands may be used. In the fluorescence detectors 32a, 32b, and 32c, photodiodes (PDs), charge coupled devices (CCDs), photo-multiplier tubes (PMTs), or the like can be used. Combinations of the wavelength selection elements and the fluorescence detectors are not limited to the three indicated herein, but one combination or two or more combinations thereof are possible.

(2) S Polarized Detector

In the fine particle measurement device according to the above-described embodiment, the example in which the image formation pattern (light reception position) on the light reception surface of the polarized light detector 51 of the S polarized component 5 in which astigmatism arises using the 4-split photodiode as the S polarized light detector 51 is acquired as the position information of the fine particles P has been described. In the fine particle measurement device according to an embodiment of the present technology, it can be considered that the fine particles P circulated in the flow passage C are directly photographed using a high-speed camera and the position information of the fine particles P is acquired through image processing.

4. Laminar Flow Monitoring Method and Laminar Flow Monitoring Program

The laminar flow monitoring method according to an embodiment of the present technology corresponds to the process performed by the determination unit of the fine particle measurement device described above. The determination unit of the fine particle measurement device stores a laminar flow monitoring program for executing this method.

The program is stored/retained in the hard disk, and loaded into the memory under control of the CPU and the OS. The program executes a process of correction. The program can be recorded on a computer-readable recording medium. The recording medium is not particularly limited as long as the recording medium is a computer-readable recording medium. Specifically, for example, a flexible disk or a disk-shaped recording medium such as a compact disc read only memory (CD-ROM) is used. In addition, a tape recording medium such as a magnetic tape may be used.

Additionally, the laminar flow monitoring method in the fine particle measurement device according to the present technology may also be configured as below.

(1)

A laminar flow monitoring method in a fine particle measurement device, the method including:

a radiation step of radiating light to a laminar flow;

a position detection step of receiving, by a detector, an S polarized component which is separated from scattered light produced from the laminar flow and to which astigmatism is given and acquiring light reception position information of the S polarized component in the detector; and a determination step of determining a state of the laminar flow based on the light reception position information.

(2)

The laminar flow monitoring method according to (1), wherein, in the position detection step, a detector of which a light reception surface is split into a plurality of regions is used as the detector.

(3)

The laminar flow monitoring method according to (2), wherein, in the position detection step, a detector of which a light reception surface is split into four regions, i.e., regions A, B, C, and D, in a lattice shape is used as the detector, and wherein a difference $\Delta 1$ (A–C) between detected values of the region A and the region C not adjacent to the region A is acquired as the light reception position information.

(4)

The laminar flow monitoring method according to (3), wherein a difference $\Delta 2$ ((A+C)–(B+D)) between a sum (A+C) of the detected values of the regions A and C and a sum (B+D) of detected values of the regions B and D is acquired as the light reception position information.

(5)

The laminar flow monitoring method according to (4), wherein, in the determination step, the state of the laminar flow is determined based on the difference $\Delta 1$ and/or the difference $\Delta 2$.

(6)

The laminar flow monitoring method according to (4) or (5), wherein, in the determination step, the laminar flow is determined to be abnormal when the difference $\Delta 1$ and/or the difference $\Delta 2$ deviates from a predetermined range, and the laminar flow is determined to be normal when the difference $\Delta 1$ and/or the difference $\Delta 2$ is included within the predetermined range.

(7)

The laminar flow monitoring method according to any one of (4) to (6), wherein, in the determination step, the laminar flow is determined to be abnormal when an acquisition frequency of the difference $\Delta 1$ and/or the difference $\Delta 2$ that deviates from the predetermined range exceeds a predetermined frequency.

(8)

The laminar flow monitoring method according to any one of (2) to (7), wherein, in the position detection step, a 4-split photodiode is used as the detector.

Additionally, the fine particle measurement device according to the present technology may also be configured as below.

(10)

A fine particle measurement device including:

a light radiation unit configured to radiate light to a laminar flow;

a first spectroscopic element configured to separate scattered light produced from the laminar flow into an S polarized component and a P polarized component;

an S polarized detector configured to receive the S polarized component;

an astigmatism element arranged between the first spectroscopic element and the S polarized detector and configured to give astigmatism to the S polarized component; and a determination unit configured to receive an output from the S polarized detector, acquire light reception position information of the S polarized component, and determine a state of the laminar flow based on the light reception position information.

(11)

The fine particle measurement device according to (10), wherein, in the S polarized detector, a light reception surface is split into four regions, i.e., regions A, B, C, and D, in a lattice shape, and wherein the determination unit acquires a difference Δ1 (A−C) between detected values of the region A and the region C not adjacent to the region A as the light reception position information.

(12)

The fine particle measurement device according to (11), wherein the determination unit acquires a difference Δ2 ((A+C)−(B+D)) between a sum (A+C) of the detected values of the regions A and C and a sum (B+D) of detected values of the regions B and D as the light reception position information.

(13)

The fine particle measurement device according to (12), wherein the determination unit determines the state of the laminar flow based on the difference Δ1 and/or the difference Δ2.

(14)

The fine particle measurement device according to (12) or (13), wherein the determination unit determines the laminar flow to be abnormal when the difference Δ1 and/or the difference Δ2 deviates from a predetermined range, and determines the laminar flow to be normal when the difference Δ1 and/or the difference Δ2 is included within the predetermined range.

(15)

The fine particle measurement device according to any one of (12) to (14), further including:

an output unit, wherein information regarding the difference Δ1 and/or the difference Δ2 is displayed in an image form on the output unit.

(16)

The fine particle measurement device according to (14) or (15), wherein abnormal determination of the laminar flow by the determination unit is presented by the output unit.

(17)

The fine particle measurement device according to any one of (14) to (16), wherein the fine particle measurement device is automatically stopped when the determination unit determines the laminar flow to be abnormal.

(18)

The fine particle measurement device according to any one of (10) to (17), wherein the astigmatism element is a cylindrical lens.

(19)

The fine particle measurement device according to any one of (10) to (18), further including:

a second spectroscopic element configured to separate light produced from the laminar flow into the scattered light and fluorescence;

a P polarized light detector configured to detect the P polarized component; and a fluorescence detector configured to detect the fluorescence.

(20)

The fine particle measurement device according to any one of (10) to (19), further including:

a third spectroscopic element configured to separate the fluorescence, wherein, in the fluorescence detector, a plurality of independent light-receiving elements that detect the fluorescence separated by the third spectroscopic element are arranged.

REFERENCE SIGNS LIST 1 excitation light
11 light source
12 objective lens
2 scattered light
21 condensing lens
22 spectroscopic element
23 spectroscopic element
3 fluorescence
31 spectroscopic element
31a, 31b, 31c wavelength selection element
32, 32a, 32b, 32c fluorescence detector
4 P polarized component
41 P polarized light detector
5 S polarized component
51 S polarized light detector
52 astigmatism element
C flow passage
L laminar flow
P fine particle
S laser spot

The invention claimed is:

1. A laminar flow monitoring method in a fine particle measurement device, the method comprising:

radiating light to a laminar flow;

receiving, by a detector of which a light reception surface is split into four regions A, B, C, and D, in a lattice shape, an S polarized component which is separated from scattered light produced from the laminar flow and to which astigmatism is given;

acquiring light reception position information of the S polarized component in the detector by calculating a difference D1 (A−C) between detected values of the region A and the region C not adjacent to the region A; and determining a state of the laminar flow based on the light reception position information.

2. The laminar flow monitoring method according to claim 1, wherein the act of acquiring the light reception information further comprises calculating a difference D2 ((A+C)−(B+D)) between a sum (A+C) of the detected values of the regions A and C and a sum (B+D) of detected values of the regions B and D.

3. The laminar flow monitoring method according to claim 2, wherein the state of the laminar flow is determined based on the difference D1 and/or the difference D2.

4. The laminar flow monitoring method according to claim 3, wherein the act of determining the state of the laminar flow further comprises determining the laminar flow to be abnormal when the difference D1 and/or the difference D2 deviates from a predetermined range, and determining the laminar flow to be normal when the difference D1 and/or the difference D2 is included within the predetermined range.

5. The laminar flow monitoring method according to claim 4, wherein the laminar flow is determined to be abnormal when an acquisition frequency of the difference D1 and/or the difference D2 that deviates from the predetermined range exceeds a predetermined frequency.

6. The laminar flow monitoring method according to claim 5, wherein the detector comprises a 4-split photodiode.

7. A fine particle analysis method comprising:

detecting light produced from a laminar flow containing fine particles;

obtaining an analysis result of optical characteristics of the fine particles based on intensity information of the light acquired in the light detection step; and performing laminar flow monitoring, comprising:
  radiating light to the laminar flow;
  receiving, by a detector of which a light reception surface is split into four regions A, B, C, and D, in a lattice shape, an S polarized component which is separated from scattered light produced from the laminar flow and to which astigmatism is given;
  acquiring light reception position information of the S polarized component in the detector by calculating a difference D1 (A−C) between detected values of the region A and the region C not adjacent to the region A; and
  determining whether a state of the laminar flow is normal based on the light reception position information,
wherein only the intensity information acquired while the laminar flow is determined to be normal is extracted and the analysis result is obtained.

8. A fine particle measurement device comprising:
a light radiation unit configured to radiate light to a laminar flow;
a first spectroscopic element configured to separate scattered light produced from the laminar flow into an S polarized component and a P polarized component;
an S polarized detector of which a light reception surface is split into four regions A, B, C, and D, in a lattice shape, the S polarized detector being configured to receive the S polarized component;
an astigmatism element arranged between the first spectroscopic element and the S polarized detector and configured to give astigmatism to the S polarized component; and
determination circuitry configured to receive an output from the S polarized detector, acquire light reception position information of the S polarized component by calculating a difference D1 (A−C) between detected values of the region A and the region C not adjacent to the region A, and determine a state of the laminar flow based on the light reception position information.

9. The fine particle measurement device according to claim 8, wherein the determination circuitry is further configured to acquire the light reception position information by calculating a difference D2 ((A+C)−(B+D)) between a sum (A+C) of the detected values of the regions A and C and a sum (B+D) of detected values of the regions B and D.

10. The fine particle measurement device according to claim 9, wherein the determination circuitry is further configured to determine the state of the laminar flow based on the difference D1 and/or the difference D2.

11. The fine particle measurement device according to claim 10, wherein the determination circuitry is further configured to determine the laminar flow to be abnormal when the difference D1 and/or the difference D2 deviates from a predetermined range, and determines the laminar flow to be normal when the difference D1 and/or the difference D2 is included within the predetermined range.

12. The fine particle measurement device according to claim 11, further comprising:
a display; and
output circuitry,
wherein the output circuitry is configured to cause the display to display information regarding the difference D1 and/or the difference D2.

13. The fine particle measurement device according to claim 12, wherein the output circuitry is configured to cause the display to display information regarding an abnormal determination of the laminar flow by the determination circuitry.

14. The fine particle measurement device according to claim 13, wherein the fine particle measurement device is configured to automatically stop when the determination circuitry determines the laminar flow to be abnormal.

15. The fine particle measurement device according to claim 14, wherein the astigmatism element is a cylindrical lens.

16. The fine particle measurement device according to claim 15, further comprising:
a second spectroscopic element configured to separate light produced from the laminar flow into the scattered light and fluorescence;
a P polarized light detector configured to detect the P polarized component; and
a fluorescence detector configured to detect the fluorescence.

17. The fine particle measurement device according to claim 16, further comprising:
a third spectroscopic element configured to separate the fluorescence,
wherein, in the fluorescence detector, a plurality of independent light-receiving elements that detect the fluorescence separated by the third spectroscopic element are arranged.

18. The fine particle measurement device according to claim 8, wherein the determination circuitry comprises a central processing unit.

19. The fine particle measurement device according to claim 12, wherein the determination circuitry and the output circuitry comprise a central processing unit.

* * * * *